A

(12) United States Patent
Arrigo et al.

(10) Patent No.: US 9,125,684 B2
(45) Date of Patent: Sep. 8, 2015

(54) INTRODUCER FOR RADIOFREQUENCY NEEDLE

(75) Inventors: Anthony C. Arrigo, North Andover, MA (US); Thomas Simopoulos, Southborough, MA (US); Raymond T. Charbonneau, Swansea, MA (US)

(73) Assignee: Spectra Medical Devices, Inc., Wilmington, MA (US)

( * ) Notice: Subject to any disclaimer, the term of this patent is extended or adjusted under 35 U.S.C. 154(b) by 714 days.

(21) Appl. No.: 13/286,599

(22) Filed: Nov. 1, 2011

(65) Prior Publication Data

US 2013/0046294 A1     Feb. 21, 2013

Related U.S. Application Data

(60) Provisional application No. 61/525,122, filed on Aug. 18, 2011.

(51) Int. Cl.
*A61B 17/00* (2006.01)
*A61B 17/34* (2006.01)
*A61B 18/14* (2006.01)
*A61B 19/00* (2006.01)

(52) U.S. Cl.
CPC ......... *A61B 17/3417* (2013.01); *A61B 17/3403* (2013.01); *A61B 17/3415* (2013.01); *A61B 17/3401* (2013.01); *A61B 18/1477* (2013.01); *A61B 2017/00526* (2013.01); *A61B 2017/00946* (2013.01); *A61B 2017/3454* (2013.01); *A61B 2019/4805* (2013.01)

(58) Field of Classification Search
CPC ................ A61B 18/14; A61B 18/1477; A61B 2018/1425; A61B 2018/1427; A61B 17/3417

USPC .................................................. 606/32, 41, 45
See application file for complete search history.

(56) References Cited

U.S. PATENT DOCUMENTS 4,518,383 A    5/1985   Evans
5,722,955 A    3/1998   Racz
(Continued)

FOREIGN PATENT DOCUMENTS

WO    WO-98/40116 A1    9/1998
WO    WO-01/66177 A1    9/2001

OTHER PUBLICATIONS

Vesnovsky, Oleg et al., "Performance Testing of Huber Needles for Coring of Port Septa", Journal of Medical Devices, vol. 4, 031008-1-031008-7, Sep. 2010, Copyright 2010 by ASME.
(Continued)

*Primary Examiner* — Christopher D Koharski
*Assistant Examiner* — Michael Carey
(74) *Attorney, Agent, or Firm* — Foley & Lardner LLP

(57) ABSTRACT

An introducer for a radiofrequency needle includes a hollow tube. An introducer for a radiofrequency needle may also include a radiofrequency needle that extends through the hollow tube. The hollow tube includes a first portion that includes a longitudinal axis and a second portion that includes a longitudinal axis, that extends at an angle relative to the longitudinal axis of the first portion and has a distal tissue piercing tip segment and a bevel. The bevel has a heel segment in which the inner edge is rounded. The inner edge is rounded substantially continuously along the heel segment in an amount sufficient to prevent snagging of a radiofrequency needle on the inner edge as the radiofrequency needle is moved during placement.

15 Claims, 3 Drawing Sheets

(56) References Cited

U.S. PATENT DOCUMENTS

| | | |
|---|---|---|
| 5,899,891 A | 5/1999 | Racz |
| 5,993,437 A | 11/1999 | Raoz |
| 6,190,372 B1 | 2/2001 | Racz |
| 6,254,589 B1 | 7/2001 | Raoz |
| 6,371,943 B1 | 4/2002 | Racz et al. |
| 6,485,475 B1 * | 11/2002 | Chelly .......................... 604/264 |
| RE39,499 E | 2/2007 | Racz |
| 7,914,481 B1 | 3/2011 | Arrigo et al. |
| 2006/0276759 A1 * | 12/2006 | Kinast et al. .................. 604/272 |
| 2010/0249750 A1 | 9/2010 | Racz |

OTHER PUBLICATIONS

International Search Report and Written Opinion dated Feb. 15, 2012 as received in corresponding PCT Application No. PCT/US2011/058746, 7 pages.

RX Epidural Needle—Coudé®; http://www.epimedpain.com/products/needles_and_introducers/; © 2009 Epimed Pain Management Products, 5 pages.

Extended Search Report dated Apr. 24, 2015, in corresponding European application No. 11 870 939.3, 7 pages.

* cited by examiner

INTRODUCER FOR RADIOFREQUENCY NEEDLE

CROSS-REFERENCE TO RELATED PATENT APPLICATIONS

This application claims priority to and the benefit of U.S. Provisional Patent Application No. 61/525,122, filed Aug. 18, 2011, the entire disclosure of which is incorporated herein by reference.

BACKGROUND

1. Field of Embodiments

The present embodiments relate generally to an introducer for a radiofrequency needle and a method of making an introducer for a radiofrequency needle. The introducer may introduce a radiofrequency needle into a patient's body.

2. Description of Related Art

During surgical procedures to the vertebrae and other parts of a patient's body, a radiofrequency needle may be used. As it relates to the vertebrae, a radiofrequency needle may be used to selectively destroy nerves that carry pain impulses. The radiofrequency needle generates heat energy that creates a lesion on the nerve(s), such as nerve(s) of the superior hypogastrid plexus, in which the heat energy is applied to damage the nerve that carries the pain impulse. As it relates to the heart, radiofrequency needles may also be used to ablate abnormal electrical pathways in heart tissue that cause atrial fibrillation. The majority of the radiofrequency needle is covered by a protective insulation so that the heat energy only passes into the surrounding tissues from the tip of the radiofrequency needle that is in close proximity to the surrounding tissues.

Conventional radiofrequency needles are introduced into a patient's body without the use of an introducer to guide placement of the radiofrequency needle. Conventional radiofrequency needles did not use introducers because surgeons and other users of the needles thought the radiofrequency needles could be successfully placed within the body without the use of an introducer. Surgeons and other users also feared that sharp edges of the introducer would strip the protective insulation from the radiofrequency needle, thereby allowing foreign contaminants into a patient's body.

Disadvantages result when a radiofrequency needle is introduced into a patient's body without the use of an introducer. Disadvantages include the failure to accurately introduce smaller gauge needles into a patient's body. Disadvantages also include the failure to access all areas of a patient's body, such as ventral access of the vertebral body.

A need exists for an introducer for a radiofrequency needle and a method of making an introducer for a radiofrequency needle, including an introducer that addresses one or more of the above described disadvantages.

SUMMARY

One embodiment relates to an introducer for a radiofrequency needle. The radiofrequency needle comprises a hollow tube. The hollow tube includes a first portion and a second portion. The first portion includes a longitudinal axis. The second portion includes a longitudinal axis, extends at an angle relative to the longitudinal axis of the first portion and has a distal tissue piercing tip segment and a bevel. The bevel has a heel segment in which the inner edge is rounded. The inner edge is rounded substantially continuously along the heel segment in an amount sufficient to prevent snagging of a radiofrequency needle on the inner edge as the radiofrequency needle is moved during placement.

Another embodiment relates to an introducer for a radiofrequency needle. The radiofrequency needle comprises a hollow tube and a radiofrequency needle. The hollow tube includes a first portion and a second portion. The first portion includes a longitudinal axis. The second portion includes a longitudinal axis, extends at an angle relative to the longitudinal axis of the first portion and has a distal tissue piercing tip segment and a bevel. The inner edge is rounded substantially continuously along the heel segment in an amount sufficient to prevent snagging of a radiofrequency needle on the inner edge as the radiofrequency needle is moved during placement. The radiofrequency needle extends through the hollow tube.

Yet another embodiment relates to a method of making an introducer for a radiofrequency needle. The method comprises deforming a hollow tube to include a first portion having a longitudinal axis and a second portion having a longitudinal axis and that extends at an angle relative to the longitudinal axis of the first portion. The method also comprises removing material at the second portion to form a distal tissue piercing tip segment and a bevel having a heel segment and comprises treating the heel segment to prevent snagging of the radiofrequency needle.

BRIEF DESCRIPTION OF THE DRAWINGS

These and other features, aspects and advantages of the disclosed embodiments will become apparent from the following description, appended claims and the accompanying exemplary embodiments shown in the drawings, which are briefly described below.

DETAILED DESCRIPTION

Figure 1:
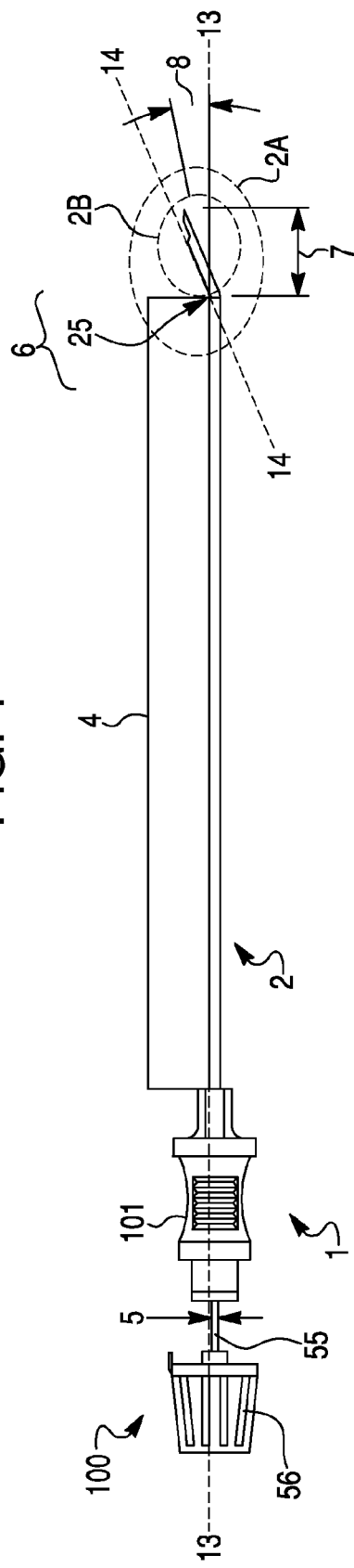
FIG. 1 is a side view of an introducer and a radiofrequency needle.

Presently preferred embodiments are illustrated in the drawings. The disclosure relates to an introducer for a radiofrequency needle and a method of making an introducer for a radiofrequency needle. The introducer may introduce the radiofrequency needle into a patient's body.

Figure 2C:
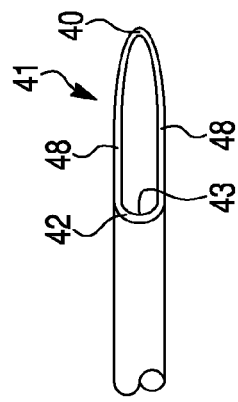
FIG. 2C is a top view of FIG. 2B.
Figure 2B:
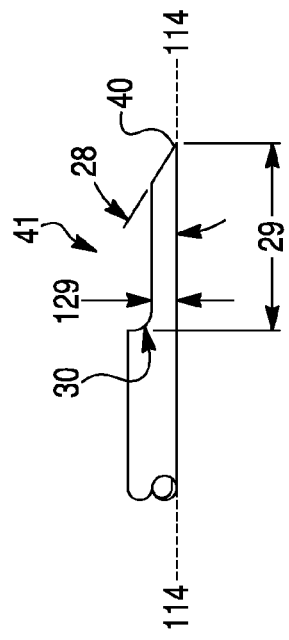
FIG. 2B is a detailed view of section 2B of FIG. 1.
Figure 2A:
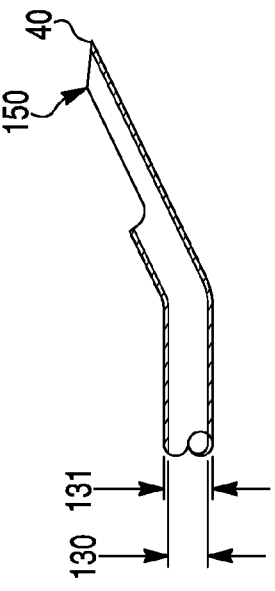
FIG. 2A is a cross-sectional view of section 2A of FIG. 1.
Figure 3:
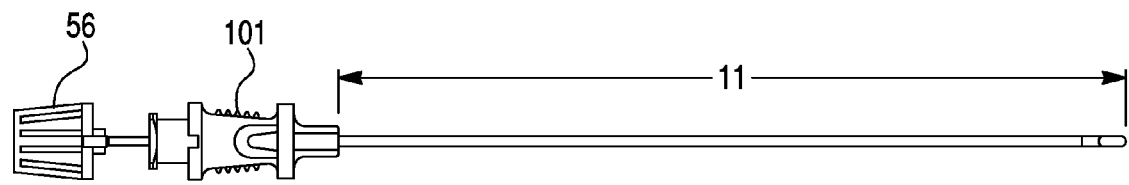
FIG. 3 is a top view of the introducer and radiofrequency needle of FIG. 1.

FIGS. 1-3 illustrate an introducer 1 for a radiofrequency needle 100. The introducer 1 includes a hollow tube 2 having a first portion 4 and a second portion 6. The first portion 4 includes a longitudinal axis 13-13 and the second portion 6 includes a longitudinal axis 14-14. The introducer 1 may be between 14 to 16 hypotubing standard gauge with a regular wall, thin wall or extra thin wall. The hollow tube 2 may be between 3 to 6 inches long. Preferably, the hollow tube 2 is 4±0.025 inches long. The inner diameter 130 of the hollow tube 2 may be between 0.045-0.073±0.002 inches and the outer diameter 131 of the hollow tube 2 may be between 0.064-0.096±0.002 inches. If the introducer 1 is 14 gauge, the inner diameter 130 of the hollow tube 2 may be between 0.0610-0.0650±0.002 inches and the outer diameter 131 of the hollow tube 2 may be between 0.0820-0.0840±0.002 inches. The inner diameter of the hollow tube 2 after molding through the hub 101 of the introducer 1 may be 0.0595±0.002 inches. If the introducer 1 is 15 gauge, the inner diameter 130 of the hollow tube 2 may be between 0.05950-0.0615±0.002 inches and the outer diameter 131 of the hollow tube 2 may be between 0.0715-0.0725±0.002 inches. The inner diameter of the hollow tube 2 after molding through the hub 101 of the introducer 1 may be 0.0570±0.002 inches. If the introducer 1 is 16 gauge, the inner diameter 130 of the hollow tube 2 may be between 0.0525-0.0545±0.002 inches and the outer diameter 131 of the hollow tube 2 may be between 0.0645-0.0655±0.002 inches. The inner diameter of the hollow tube 2 after molding through the hub 101 of the introducer 1 may be 0.0500±0.002 inches. The inner diameter of the hollow tube 2 after molding through the hub 101 is smaller than the inner diameter of the hollow tube 2 because of the material that comprises the hub. The hub 101 of the introducer 1 may be made of any suitable material, such as for example plastic (e.g. all resin types), chrome or nickel plated brass. Preferably, the hub 101 of the introducer 1 comprises plastic. The hub 101 may be 1.00±0.01 inches long. Preferably, the introducer 1 has no side ports.

The first portion 4 and the second portion 6 of the hollow tube 2 may be made of any suitable material that is malleable so that the first portion 4 and the second portion 6 may be placed at an angle to one another, and any suitable material that may be electropolished and receive a 18-24 gauge radiofrequency needle 100. For example, the first portion 4 and the second portion 6 may comprise a 304, 304L, 316, 316L stainless steel hypodermic tube or any other suitable material used to manufacture a needle, such as for instance nitinol. The first portion 4 and the second portion 6 preferably comprise the same material.

The hollow tube 2 is bent such that the longitudinal axis 14-14 of the second portion 6 extends at an angle 8 relative to the longitudinal axis 13-13 of the first portion 4. The bend length 7, where the bend length 7 is the length of the second portion 6 of the hollow tube 2, may be 0.900±0.050 inches. The angle 8 makes it easier for the introducer 1 to enter a patient's body and to facilitate passage of the radiofrequency needle 100 around a bone. For example, the angle 8 facilitates ventral access of the vertebral body for the radiofrequency needle. The angle 8 may range from approximately 15° and 21° or from 15° and 21°. Preferably, the angle 8 is 18° or is approximately 18°. The radius 25 between the first portion 4 and the second portion 6 when the longitudinal axis 14-14 of the second portion 6 is at an angle 8 relative to the longitudinal axis 13-13 of the first portion 4 may be 1.040 inches or approximately 1.040 inches.

As shown in FIGS. 2A-2C, the second portion 6 may include a distal tissue piercing tip segment 40 and a bevel 41. The distal tissue piercing tip segment is at an angle 28 (FIG. 2B) to a second longitudinal axis 114-114 of the second portion 6 of the hollow tube 2 and has a radius of 0.010 inches or approximately 0.010 inches (FIG. 2A). The angle may be any suitable angle 28. For example, the angle 28 may be approximately 15° to approximately 30° or 15° to 30° for better penetration of the distal tissue piercing tip segment 40. Preferably, the angle is 30° or is approximately 30. The bevel 41 may include a pair of parallel, longitudinally extending sides 48, the distal tissue piercing tip segment 40 and a heel segment 42 where the longitudinally extending sides 48 connect the distal tissue piercing tip segment 40 to the heel segment 42. The length 29 of the bevel may be between 0.18-0.48 inches and is preferably 0.28 inches or approximately 0.28 inches for a 14 gauge introducer 1. The length 29 of the bevel may be between 0.15-0.45 inches and is preferably 0.25 inches or approximately 0.25 inches for a 15 gauge introducer 1. The length 29 of the bevel may be between 0.12-0.42 inches and is preferably 0.22 inches or approximately 0.22 inches for a 16 gauge introducer 1. The thickness 129 of the bevel may be between 0.042 and 0.047±0.005 inches for a 14 gauge introducer 1, 0.036 and 0.041±0.005 inches for a 15 gauge introducer 1 and 0.032 and 0.037±0.005 inches for a 16 gauge introducer.

The heel segment 42 is semi-circularly shaped and includes an inner edge 43 that is rounded continuously or substantially continuously along the heel segment 42. The radius 30 of the heel segment 42 may be between 0.025 and 0.035 inches ±0.005 inches. For example, the radius 30 of the heel segment 42 for a 14 gauge introducer may be 0.035 inches ±0.005 inches, the radius 30 of the heel segment 42 for a 15 gauge introducer may be 0.030 inches ±0.005 inches and the radius 30 of the heel segment 42 for a 16 gauge introducer may be 0.025 inches ±0.005 inches. The inner edge 43 is rounded to an amount that is sufficient to prevent snagging of the radiofrequency needle 100 on the inner edge 43 when the radiofrequency needle 100 is moved during placement of the radiofrequency needle 100 into the introducer 1.

The inner edge 43 of the heel segment 42 may be rounded by electropolishing. The inner edge 43 of the heel segment 42 may be electropolished in a controlled manner, with the electropolishing process being focused on the heel segment 42 of the bevel 41 such that the inner edge 43 of the heel segment 42 is formed with a regular and uniform cross-sectional radius large enough to avoid catching of the radiofrequency needle 100 on irregular transitional regions of the hollow tube 2 of the introducer 1. Preferably the inner edge 43 of the heel segment 42 is electropolished to a radius of at least about 0.002 inch ±0.005 inches. Electropolishing of the inner edge 43 to such a radius is sufficient to materially reduce the risk of, and possibly avoid, adverse interference between the heel segment 42 and the outer surfaces of the radiofrequency needle 100.

The introducer 1 may also include a radiofrequency needle 100 that extends through the hollow tube 2. The outer diameter 5 of the radiofrequency needle 100 may be any suitable diameter. For example, the outer diameter 5 of the radiofrequency needle 100 may be 0.056±0.002 inches, 0.053±0.002 inches or 0.046±0.002 inches. The radiofrequency needle 100 includes a protective insulation 55 and a tip (not shown). The insulation 55 covers the outer surface of a majority of the radiofrequency needle 100. The insulation 55 does not protrude past the tip of the radiofrequency needle 100. The insulation 55 protects the tissue that surrounds the radiofrequency needle 100 by ensuring that heat energy does not pass into the surrounding tissue. The insulation 55 may be made of any material that is capable of ensuring that electric current does not pass through the insulation 55 into the surrounding tissue. For example, the insulation may be polypropylene. The internal components of the radiofrequency needle 100 may include conventional components.

A cap 56 of an introducer 1 may be at an end of the introducer 1 and opposite to the tip of the radiofrequency needle 100 that ablates tissue. The cap 56 may be made of any suitable material, such as for example plastic (e.g. polypropylene), chrome or nickel plated brass. The cap 56 to insulation 55 bond may withstand an axial pull force of at least 5 pounds and the hub 101 to needle 100 bond may withstand an axial pull force of at least 15 pounds.

Figure 5:
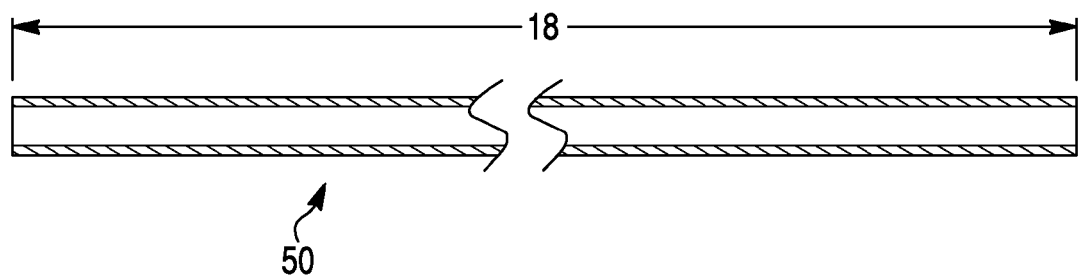
FIG. 5 is a cross-sectional view of a sheath that may be placed over a portion of the introducer of FIG. 1.

The hollow tube 2 of the introducer 1 may be covered by a sheath 50 (FIG. 5) while not in use. The sheath 50 may be made of any suitable material. For example, the sheath 50 may be made of low-density polyethylene (LDPE) or another plastic. The sheath 50 may be any suitable length and is preferably longer than the hollow tube 2. For example, the sheath 50 may be approximately 4.5 inches or 4.5 inches when the hollow tube 2 is approximately 4 inches or 4 inches long.

Figure 6:
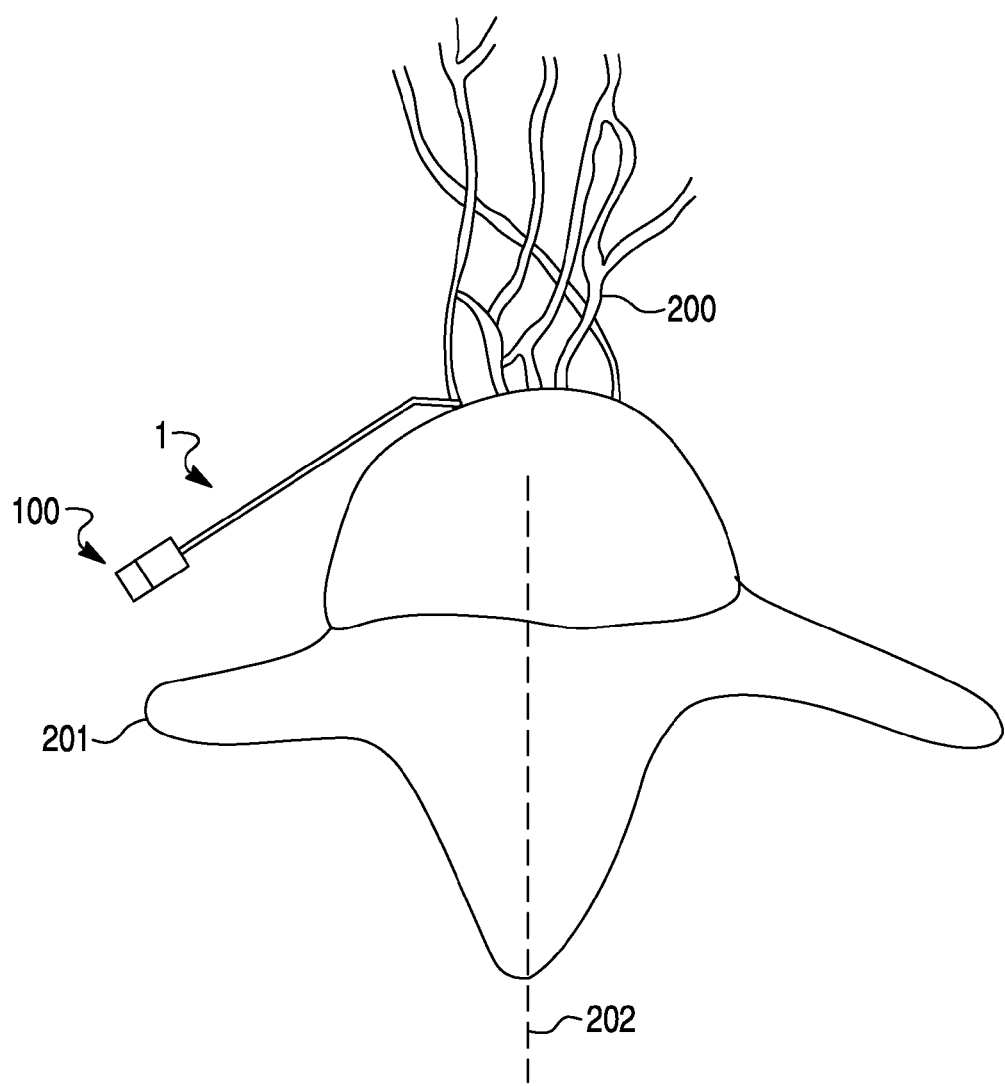
FIG. 6 is a side view of a portion of the vertebrae with an introducer and radiofrequency needle in close proximity to the superior hypogastrid plexus.

As shown in FIG. 6, the introducer 1 may access the anterior vertebral body 201 to ablate nerve(s) of the superior hypogastrid plexus 200. The introducer 1 is capable of allowing the radiofrequency needle 100 to reach the mid point 202 of the vertebral body 201, so that the radiofrequency needle 100 can reach tissue that conventional radiofrequency needles cannot reach or have difficulty reaching. The introducer 1 is also capable of allowing the radiofrequency needle 100 around bone so that the radiofrequency needle 100 can reach tissue that conventional radiofrequency needles cannot reach or have difficulty reaching. The angle 8 of the introducer 1 allows the radiofrequency needle 100 to reach tissue and reach around bone that conventional radiofrequency needles cannot reach.

A method of making the introducer 1 for the radiofrequency needle 100 includes deforming the hollow tube 2 to include the first portion 4 having the longitudinal axis 13-13 and the second portion 6 having the longitudinal axis 14-14 that extends at an angle 8 relative to the longitudinal axis 13-13 of the first portion 4. The hollow tube 2 may be deformed by any suitable mechanism. To aid in deforming the hollow tube 2, the hollow tube 2 comprises a material, such as the aforementioned disclosed materials, that can be deformed by the suitable mechanism. The first portion 4 and the second portion 6 of the hollow tube 2 could be integrally formed. Alternatively, the first portion 4 and the second portion 6 could be separate components joined together, but this is not preferred.

The method of making the introducer 1 also includes removing material at the second portion 6 to form the distal tissue piercing tip segment 40 and the bevel 41 having the heel segment 42. The material may be removed by any suitable mechanism. For example, the material may be removed by grinding or electrical discharge machining (EDM). When the material is removed, the inner edge 43 of the heel segment 42 that results from the grinding of the bevel 41 is susceptible to having burrs and/or other irregular edges. The radiofrequency needle 100 may be snagged on the burrs and/or other irregular edges when the radiofrequency needle 100 is introduced through the introducer 1.

To prevent snagging of the radiofrequency needle 100, the method of making the introducer 1 includes treating the heel segment 42. Electropolishing may be used to treat the heel segment 42. Treatment by electropolishing provides a substantially continuously rounded inner edge 43 of the heel segment 42.

Figure 4:
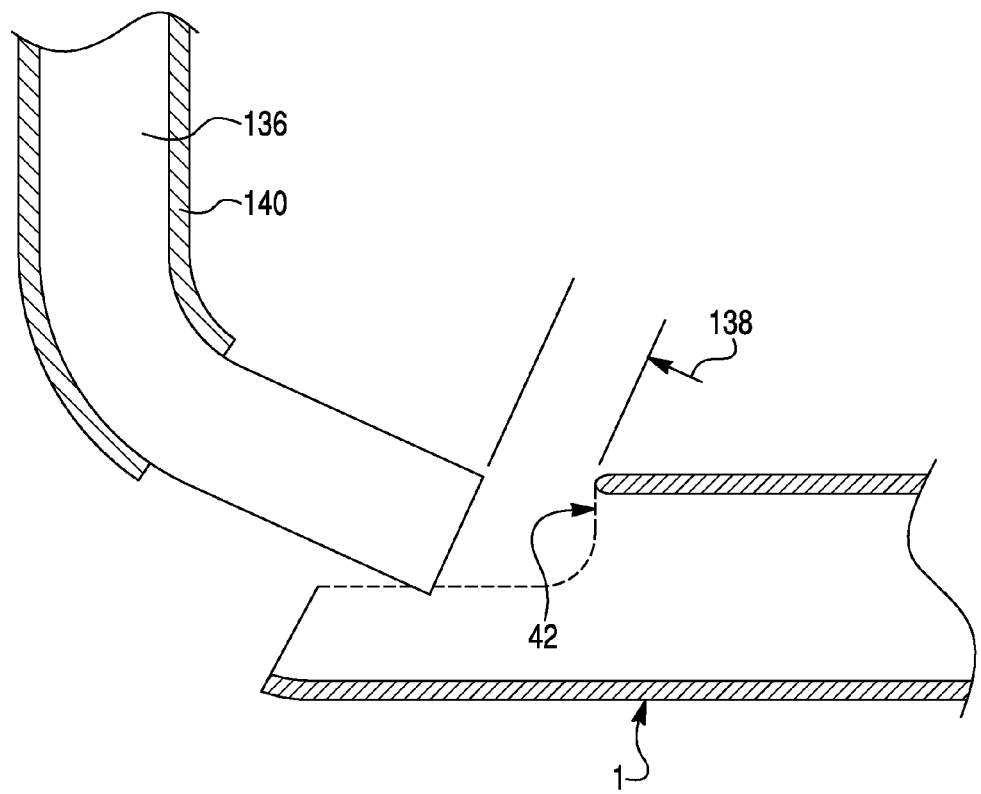
FIG. 4 is a diagrammatic, cross-sectional illustration of the arrangement for electropolishing portions of the introducer.

FIG. 4 illustrates in diagrammatic side view the manner in which the electropolishing may be conducted. The electropolishing is conducted using a wire-like electrode (cathode) 136 that is contained within an insulative jacket 140. The electrode 136 may be formed from any suitable material. For example, the electrode 136 may be formed of titanium or copper.

During electropolishing, the introducer 1 and the electrode 136 may be held in a fixture (not shown). The fixture supports the electrode 136 and introducer 1 in a relative orientation that will concentrate the energy applied between the electrode 136 and the introducer 1 so that the electrode 136 is at its greatest intensity at the region of the heel segment 42.

During electropolishing, the electrode 136 may be configured and positioned to provide substantially uniform energy density along the inner edge 43 of the heel segment 42 to obtain a substantially continuous electropolished radius along the inner edge 43 of the heel segment 42. The tip of the electrode 136 may be directed toward the heel segment 42 and may be held at a desired distance 138 from the heel segment 32. Preferably, the desired distance 138 ranges from approximately 2 to 3 millimeters. To ensure that the electrode 136 can be placed in close proximity to the heel segment 42, the electrode includes a diameter that is no greater and, preferably, smaller than the inner diameter of the introducer 1.

Also during electropolishing, the introducer 1 and the electrode 136 may be immersed within any suitable electropolishing fluid for use with the material that comprises the introducer 1. An example of suitable electropolishing fluid includes 300 series stainless steel. The duration, voltages, electric current, temperature and specific gravity of the electropolishing fluid may vary. These parameters may be varied such that the electropolishing of the introducer 1 is completed in approximately two and a half minutes to result in a substantially continuous radius along the inner edge 43 of the heel segment 42. Although, FIG. 4 only shows one electrode 136, a plurality of electrodes may be provided to conduct the electropolishing of one or more introducers in batch quantities with substantially greater efficiency and uniformity of results than with conventional abrading techniques.

* * *

As utilized herein, the terms "approximately," "about," "substantially" and similar terms are intended to have a broad meaning in harmony with the common and accepted usage by those of ordinary skill in the art to which the subject matter of this disclosure pertains. It should be understood by those of skill in the art who review this disclosure that these terms are intended to allow a description of certain features described and claimed without restricting the scope of these features to the precise numerical ranges provided. Accordingly, these terms should be interpreted as indicating that insubstantial or inconsequential modifications or alterations of the subject matter described and are considered to be within the scope of the disclosure.

It should be noted that the term "exemplary" as used herein to describe various embodiments is intended to indicate that such embodiments are possible examples, representations, and/or illustrations of possible embodiments (and such term is not intended to connote that such embodiments are necessarily extraordinary or superlative examples).

For the purpose of this disclosure, the term "coupled" means the joining of two members directly or indirectly to one another. Such joining may be stationary or moveable in nature. Such joining may be achieved with the two members or the two members and any additional intermediate members being integrally formed as a single unitary body with one another or with the two members or the two members and any additional intermediate members being attached to one another. Such joining may be permanent in nature or may be removable or releasable in nature.

It should be noted that the orientation of various elements may differ according to other exemplary embodiments, and that such variations are intended to be encompassed by the present disclosure. It is recognized that features of the disclosed embodiments can be incorporated into other disclosed embodiments.

It is important to note that the constructions and arrangements of the introducer for a radiofrequency needle or components thereof as shown in the various exemplary embodiments are illustrative only. Although only a few embodiments have been described in detail in this disclosure, those skilled in the art who review this disclosure will readily appreciate that many modifications are possible (e.g., variations in sizes, dimensions, structures, shapes and proportions of the various elements, values of parameters, mounting arrangements, use of materials, colors, orientations, etc.) without materially departing from the novel teachings and advantages of the subject matter recited in the claims. For example, elements shown as integrally formed may be constructed of multiple parts or elements, the position of elements may be reversed or otherwise varied, and the nature or number of discrete elements or positions may be altered or varied. The order or sequence of any process or method steps may be varied or re-sequenced according to alternative embodiments. Other substitutions, modifications, changes and omissions may also be made in the design, operating conditions and arrangement of the various exemplary embodiments without departing from the scope of the present disclosure.

What is claimed is:

1. An introducer for a radiofrequency needle, comprising:
   a hollow tube that includes:
     a first portion including a longitudinal axis; and
     a second portion including a longitudinal axis and that extends at an angle relative to the longitudinal axis of the first portion,
   wherein the second portion includes a distal tissue piercing tip segment, a bevel, and a circumferential wall,
   wherein the bevel has a heel segment in which an inner edge is rounded, wherein the inner edge is rounded substantially continuously along the heel segment in an amount sufficient to prevent snagging of a radiofrequency needle on the inner edge as the radiofrequency needle is moved during placement,
   wherein the circumferential wall extends parallel to the longitudinal axis of the second portion and is configured to extend completely around a perimeter of the radiofrequency needle in a plane orthogonal to the longitudinal axis of the second portion.

2. The introducer of claim 1, wherein the inner edge of the heel segment is rounded by electropolishing.

3. The introducer of claim 2, wherein the rounded inner edge of the heel segment includes a radius of approximately 0.002 inches extending substantially continuously around the heel segment.

4. The introducer of claim 1, wherein the distal tissue piercing tip segment is at an angle to the longitudinal axis of the second portion.

5. The introducer of claim 4, wherein the angle is approximately 30°.

6. The introducer of claim 1, wherein the angle is between approximately 15° and 21°.

7. The introducer of claim 6, wherein the angle is approximately 18°.

8. An introducer for a radiofrequency needle, comprising:
   a hollow tube that includes:
     a first portion including a longitudinal axis; and
     a second portion including a longitudinal axis and that extends at an angle relative to the longitudinal axis of the first portion,
   wherein the second portion includes a distal tissue piercing tip segment, a bevel, and a circumferential wall; and
   a radiofrequency needle that extends through the hollow tube,
   wherein the bevel has a heel segment in which an inner edge is rounded, wherein the inner edge is rounded substantially continuously along the heel segment in an amount sufficient to prevent snagging of the radiofrequency needle on the inner edge as the radiofrequency needle is moved during placement,
   wherein the circumferential wall extends parallel to the longitudinal axis of the second portion and is configured to extend completely around a perimeter of the radiofrequency needle in a plane orthogonal to the longitudinal axis of the second portion.

9. A method of making an introducer for a radiofrequency needle, comprising:
   deforming a hollow tube to include a first portion having a longitudinal axis and a second portion having a longitudinal axis and that extends at an angle relative to the longitudinal axis of the first portion;
   removing material at the second portion to form a distal tissue piercing tip segment and a bevel having a heel segment; and
   treating the heel segment to prevent snagging of the radiofrequency needle,
   wherein the second portion includes a circumferential wall that extends parallel to the longitudinal axis of the second portion and is configured to extend completely around a perimeter of the radiofrequency needle in a plane orthogonal to the longitudinal axis of the second portion.

10. The method of claim 9, wherein the step of treating includes electropolishing an inner edge of the heel segment to provide a substantially continuously rounded inner edge of the heel segment.

11. The method of claim 9, wherein the distal tissue piercing tip segment is at an angle to the longitudinal axis of the second portion.

12. The method of claim 11, wherein the angle is between approximately 15° and 30°.

13. The method of claim 12, wherein the angle is approximately 30°.

14. The method of claim 9, wherein the angle is between approximately 15° and 21°.

15. The method of claim 14, wherein the angle is approximately 18°.

* * * * *